(12) United States Patent
Castells Garangou et al.

(10) Patent No.: US 12,668,846 B2
(45) Date of Patent: Jun. 30, 2026

(54) NON-INVASIVE METHOD FOR THE DIAGNOSIS OR SCREENING OF COLORECTAL CANCER AND/OR PRE-CANCEROUS STAGE THEREOF

(71) Applicants: INSTITUT D'INVESTIGACIONS BIOMÈDIQUES AUGUST PI I SUNYER (IDIBAPS), Barcelona (ES); HOSPITAL CLÍNIC DE BARCELONA, Barcelona (ES); CONSORCIO CENTRO DE INVESTIGACIÓN BIOMÉDICA EN RED, Madrid (ES); UNIVERSITAT DE BARCELONA, Barcelona (ES)

(72) Inventors: Antoni Castells Garangou, Barcelona (ES); Meritxell Gironella Cos, Barcelona (ES); Saray Duran Sanchon, Barcelona (ES)

(73) Assignees: HOSPITAL CLÍNIC DE BARCELONA, Barcelona (ES); UNIVERSITAT DE BARCELONA, Barcelona (ES); INSTITUT D'INVESTIGACIONS BIOMÈDIQUES AUGUST PI I SUNYER (IDIBAPS), Barcelona (ES); CONSORCIO CENTRO DE INVESTIGACIÓN BIOMÉDICA EN RED, Madrid (ES)

( * ) Notice: Subject to any disclaimer, the term of this patent is extended or adjusted under 35 U.S.C. 154(b) by 1109 days.

(21) Appl. No.: 17/625,547

(22) PCT Filed: Jul. 14, 2020

(86) PCT No.: PCT/EP2020/069918
§ 371 (c)(1),
(2) Date: Jan. 7, 2022

(87) PCT Pub. No.: WO2021/009184
PCT Pub. Date: Jan. 21, 2021

(65) Prior Publication Data
US 2022/0333205 A1       Oct. 20, 2022

(30) Foreign Application Priority Data
Jul. 15, 2019     (EP) ..................................... 19382597

(51) Int. Cl.
*C12Q 1/6886*          (2018.01)

(52) U.S. Cl.
CPC ..... *C12Q 1/6886* (2013.01); *C12Q 2600/178* (2013.01)

(58) Field of Classification Search
CPC ........................ C12Q 1/6886; C12Q 2600/178
See application file for complete search history.

(56) References Cited

U.S. PATENT DOCUMENTS 9,074,206 B2     7/2015 Wu
2012/0088687 A1     4/2012 Goel

OTHER PUBLICATIONS

C. Wu et al. Curr Colorectal Cancer Rep 13;481-488 (Nov. 2017). (Year: 2017).*

(Continued)

*Primary Examiner* — Diana B Johannsen
(74) *Attorney, Agent, or Firm* — Chrisman Gallo Tochtrop LLC

(57)          ABSTRACT

Non-invasive method for the diagnosis or screening of colorectal cancer and/or pre-cancerous stage thereof. The present invention refers to an in vitro method for the diagnosis of colorectal cancer and/or pre-cancerous stage thereof.

17 Claims, 4 Drawing Sheets

(56)                    References Cited

OTHER PUBLICATIONS

Tinmouth, J. et al. Gut 64:1327-1337 (Jun. 2015). (Year: 2015).*
International Search Report and Written Opinion for corresponding
international application No. PCT/EP2020/069918, dated Oct. 21,
2020. 17 pages.
Toiyama Yuji et al: DNA methylation and microRNA biomarkers
for noninvasive detection of gastric and colorectal cancer, Bio-
chemical Ano Biophysical Research Communications, Elsevier,
Amsterdam, NL, vol. 455, No. 1 , Aug. 13, 2014 (Aug. 13, 2014),
pp. 43-57. 38 p. .
To Yau et al: microRNA-221 and microRNA-18a identification in
stool as potential biomarkers for the non-invasidiagnosis of colorectal
carcinoma, British Journal of Cancer, vol. 111, No. 9, Sep. 18, 2014
(Sep. 18, 2014), pp. 1765-1771. 7 pages.
Saray Duran-Sanchon et al: "Identification and validation of microRNA
profiles in fecal samples for detection of colorectal cancer", Gas-
troenterology: Official Publication of the American Gastroenterologi-
cal Association, Oct. 1, 2019. 15 pages.
Shirafkan Naghmeh et al: "MicroRNAs as novel biomarkers for
colorectal cancer: New outlooks", Biomedicine and Pharmacotherapy,
Elsevier, FR, vol. 97, Nov. 14, 2017. 12 pages.
Yang Xiaoyu et al: "The expression and clinical significance of
microRNAs in colorectal cancer detecting", Tumor Biology, Karger,
Basel, CH, vol. 36, No. 4, Dec. 6, 2014. 10 pages.
Rotelli MT et al: "Fecal microRNA profile in patients with colorectal
carcinoma before and after curative surgery", International Journal
of Colorectal Disease, Springer Verlag, Berlin, DE, vol. 30, No. 7,
May 20, 2015. 8 pages.

* cited by examiner

A)

B)

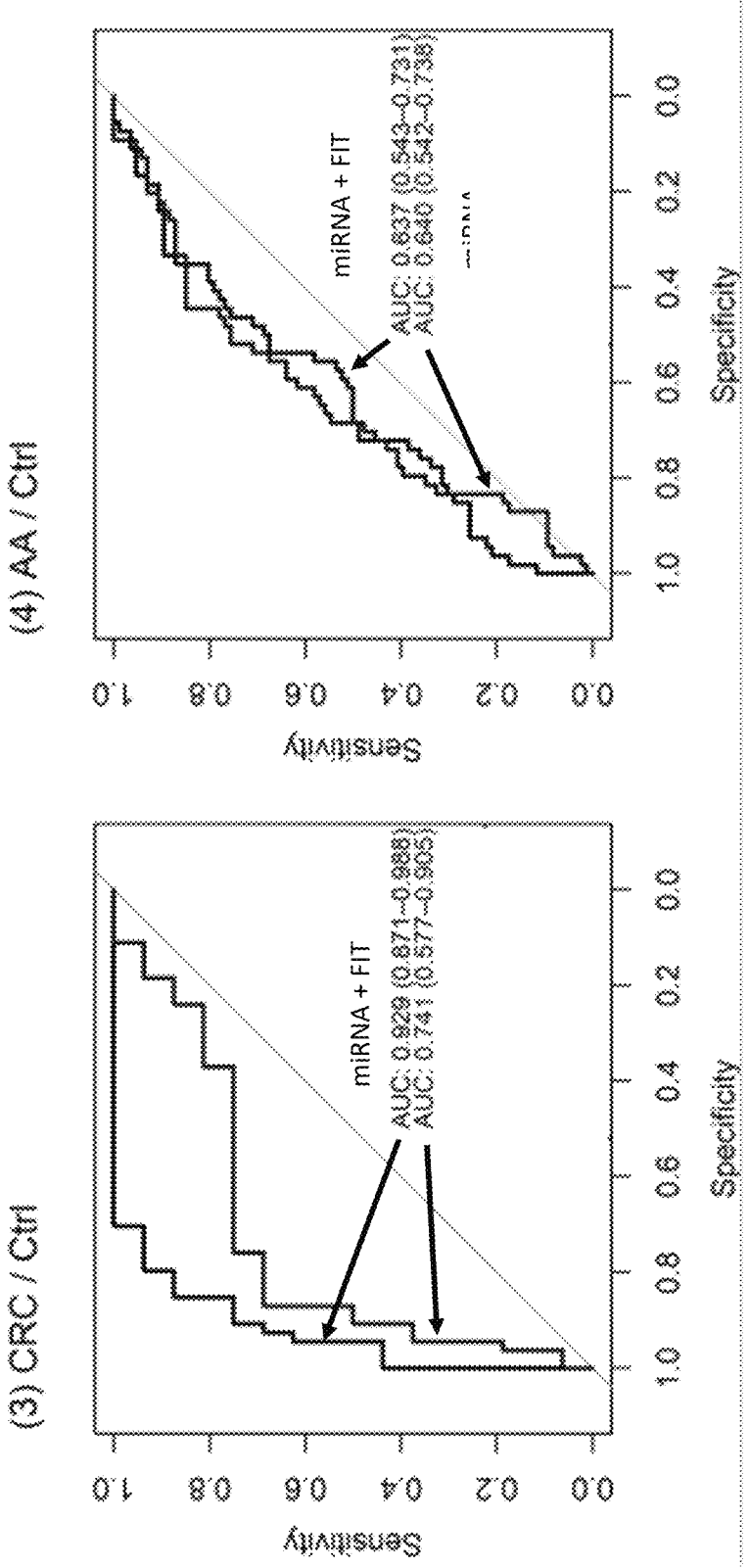
Figure 3 (continuation)

NON-INVASIVE METHOD FOR THE DIAGNOSIS OR SCREENING OF COLORECTAL CANCER AND/OR PRE-CANCEROUS STAGE THEREOF

CROSS-REFERENCE TO RELATED PATENT APPLICATIONS

This application is a U.S. National Stage Application under 35 U.S.C. § 371 of International Patent Application No. PCT/EP2020/069918 filed Jul. 14, 2020, which claims the benefit of priority of European Patent Application No. 19382597.3 filed Jul. 15, 2019, both of which are incorporated by reference in their entireties. The International Application was published on Jan. 21, 2021, as International Publication No. WO 2021/009184 A1.

FIELD OF THE INVENTION

The present invention can be included in the medical field. Particularly, the present invention refers to an in vitro method for the diagnosis or screening of colorectal cancer and/or pre-cancerous stage thereof.

STATE OF THE ART

Colorectal cancer (CRC) (also known as colon cancer, rectal cancer, or bowel cancer) is the development of cancer in the colon or rectum (parts of the large intestine). The vast majority of colorectal cancers are adenocarcinomas. This is because the colon has numerous glands within the tissue. When these glands undergo a number of changes at the genetic level, they proceed in a predictable manner as they move from benign to an invasive, malignant colon cancer. The adenomas of the colon, particularly advanced colorectal adenoma (AA), are a benign version of the malignant adenocarcinomas but still with malignant potential if not removed (they are usually removed because of their tendency to become malignant and to lead to colon cancer).

Screening is an effective way for preventing and decreasing deaths from colorectal cancer and is recommended starting from the age of 50 to 75. The best known and most frequently used screening test for colorectal cancer is called Fecal Immunochemical Test (FIT). FIT is used to screen for CRC by detecting small amounts of blood in stool samples using antibodies specific to human haemoglobin. FIT detects blood in the stool samples which can be a sign of pre-cancer or cancer. If abnormal results are obtained, usually a colonoscopy is recommended which allows the physician to look at the inside of the colon and rectum to make a diagnosis. During colonoscopy, small polyps may be removed if found. If a large polyp or tumor is found, a biopsy may be performed to check if it is cancerous. The gastroenterologist uses a colonoscopy to find and remove these adenomas and polyps to prevent them from continuing to acquire genetic changes that will lead to an invasive adenocarcinoma.

Although, as explained above, FIT is nowadays used for screening colorectal cancer, it is important to note that FIT offers a low sensitivity for AA (around 20-30% depending on literature) which means that most of said kind of patients can be wrongly classified as not having the disease. Consequently, FIT is not able to identify adenomas due to its low sensitivity. On the other hand, colonoscopy is an invasive technique wherein the most severe complication generally is the gastrointestinal perforation. Moreover, colonoscopy is nowadays a procedure involving anesthesia, and the laxatives which are usually administered during the bowel preparation for colonoscopy are associated with several digestive problems.

It is important to note that the methods used today for screening general population at risk of suffering for CRC or AA are associated with a high rate of false positives. Consequently a high amount of unnecessary follow-up colonoscopies are nowadays performed.

The present invention offers a clear solution to the problems cited above because it is focused on an in vitro method for identifying or screening human subjects at risk of suffering from colorectal cancer or colorectal adenomas (particularly advanced colorectal adenomas), departing from the expression level of miRNAs. Moreover, the method of the invention offers high sensitivity and specificity, which means that it is a strong and cost-effective method for the detection of both colorectal cancer and colorectal adenomas.

DESCRIPTION OF THE INVENTION

The present invention refers to an in vitro method for diagnosing, identifying or screening human subjects at risk of suffering from colorectal cancer and/or advanced colorectal adenomas, departing from the expression level of miRNAs isolated from non-invasive samples such as stool samples. The method of the invention offers high sensitivity and specificity, which means that it is a strong and cost-effective method for the detection of both colorectal cancer and colorectal adenomas.

Since the method of the invention has higher sensitivity and specificity as compared to the method used today (FIT) for screening general population at risk of suffering from CRC or AA, it is associated with a lower percentage of false positives. Consequently, the method described in the present invention clearly helps in reducing the number of follow-up colonoscopies, thus improving the way that the patients are nowadays screened or diagnosed. Once the method of the invention is performed, if it is determined that the patients might be suffering from colorectal cancer and/or precancerous stage, the result is confirmed by colonoscopy. However, if it is not determined that the patient might be suffering from colorectal cancer and/or precancerous stage, there is no need to perform a colonoscopy and routine testing with the method of the invention defined below is recommended.

Specifically, the study comprised four stages: discovery phase by genome-wide miRNA expression profiling in 124 paired normal-tumour tissues (30 CRC; 32 AA); technical validation of miRNA candidates by qRT-PCR in faecal samples from a subset of patients included in the discovery phase (n=39) as well as control individuals (n=39); clinical validation of the most significantly up-regulated miRNAs by qRT-PCR in an independent set of faecal samples (n=767) obtained from FIT-positive participants in a CRC screening program; and development of a miRNA-based predictive model to identify patients with advanced neoplasms (i.e. CRC or AA).

Among 200 and 324 miRNAs significantly deregulated respectively in CRC and AA tissue samples, 7 and 5 were technically validated in stool samples. Of them, miR-421, miR-130b-3p and miR-27a-3p were confirmed up-regulated in patients with advanced neoplasms. Thus, a fecal miRNA signature including miR-421 and miR-27a-3p was more accurate than fecal haemoglobin concentration (AUC=0.63 vs. 0.59, respectively) to discriminate these patients from individuals with normal colonoscopy, whereas combination of both approaches achieved the highest accuracy for such a purpose (AUC=0.67).

Thus, the first embodiment of the present invention refers to an in vitro method (hereinafter "method of the invention") for the diagnosis or screening colorectal cancer and/or a pre-cancerous stage thereof which comprises: a) Measuring the expression level of at least miR-421 and/or miR-130b and/or miR-27a, in a biological sample obtained from the subject and b) wherein the overexpression of miR-421 and/or miR-130b and/or miR-27a, as compared with the reference expression level measured in healthy control subjects, is indicative that the subject is suffering from colorectal cancer and/or a pre-cancerous stage thereof.

In a preferred embodiment, the method comprises: a) Measuring the expression level of at least the combination [miR-421 and miR-27a], [miR-421 and miR-25], [miR-421 and miR-221], [miR-421 and miR-34a], [miR-421 and miR-29a] or [miR-421 and miR-130b] in a biological sample obtained from the subject and b) wherein the overexpression at least one of the combinations of miRNAs as compared with the reference expression level measured in healthy control subjects, is indicative that the subject is suffering from colorectal cancer and/or a pre-cancerous stage.

The statistical results of logistic regression obtained by using miR-421 or the combinations [miR-421 and miR-27a], [miR-421 and miR-25], [miR-421 and miR-221], [miR-421 and miR-34a], [miR-421 and miR-29a] or [miR-421 and miR-130b] are summarized in Table 1.

In a preferred embodiment, the method comprises: a) Measuring the expression level of at least the combination [miR-130b and miR-27a], [miR-130b and miR-25], [miR-130b and miR-221], [miR-130b and miR-34a] or [miR-130b and miR-29a] in a biological sample obtained from the subject and b) wherein the overexpression at least one of the combinations of miRNAs as compared with the reference expression level measured in healthy control subjects, is indicative that the subject is suffering from colorectal cancer and/or a pre-cancerous stage.

The statistical results of logistic regression obtained by using miR-130b or the combinations [miR-130b and miR-27a], [miR-130b and miR-25], [miR-130b and miR-221], [miR-130b and miR-34a] or [miR-130b and miR-29a] are summarized in Table 2.

In an embodiment of the first aspect of the invention, optionally in combination with any of the embodiments provided above or below, miR-27a is miR-27a-3p; and/or miR-25 is miR-25-3p; and/or miR-221 is miR-221-3p; and/or miR-34a is miR-34a-5p; and/or miR-29a is miR-29a-3p; and/or miR-130b is miR-130b-3p, or any of their combinations.

Such as it is shown in Table 1 and Table 2, in a preferred embodiment, the method further comprises the determination of the age and gender of the subject, preferably before the determination of the expression level of the miRNAs. So, in a preferred embodiment the method of the invention is performed in subjects at risk of suffering CRC or AA, preferably population having between 50 and 75 years old.

In an embodiment of the first aspect of the invention, optionally in combination with any of the embodiments provided above or below, the method is performed in a male or female of any age, for example, of at least 20, 25, 30, 35, 40, 45, 50, 55, 60, 65, 70, 75, 80, 85 or 90 years-old.

In a preferred embodiment, the method further comprises determining the presence or concentration of haemoglobin preferably before the determination of the expression level of the miRNAs, wherein the presence or higher concentration of haemoglobin as compared with healthy control subjects, is indicative that the subject is suffering from colorectal cancer and/or a pre-cancerous stage.

In an embodiment of the first aspect of the invention, optionally in combination with any of the embodiments provided above or below, the biological sample is a stool, blood, serum or plasma sample.

In an embodiment of the first aspect of the invention, optionally in combination with any of the embodiments provided above or below, the biological sample is a stool sample.

In a preferred embodiment, the method of the invention is performed in stool samples, preferably stool samples of less than 10 mg, preferably less than 5 mg, more preferably 2.5 mg. In fact, a clear advantage of the method of the invention is that it can be carried out by using a small amount of stool samples. Please note that commercial tests like Cologuard® requires the use of a high amount of stool samples, typically around 50 gr. Since the method of the invention can be performed using a small amount of stool samples, the determination of the expression level of the miRNAs can be carried out in the remaining stool samples which have been previously used for the determination of the presence or concentration of haemoglobin.

In an embodiment of the first aspect of the invention, optionally in combination with any of the embodiments provided above or below, the method comprises: a) measuring the expression level of at least miR-421 and determining the presence or concentration of haemoglobin in a stool sample obtained from the subject, and b) wherein the overexpression of miR-421, as compared with the reference expression level measured in healthy control subjects and wherein the presence or higher concentration of haemoglobin as compared with healthy control subjects is indicative that the subject is suffering from colorectal cancer and/or a pre-cancerous stage thereof.

In an embodiment of the first aspect of the invention, optionally in combination with any of the embodiments provided above or below, the method comprises: a) measuring the expression level of at least the combination [miR-421 and miR-27a], [miR-421 and miR-25], [miR-421 and miR-221], [miR-421 and miR-34a], [miR-421 and miR-29a] or [miR-421 and miR-130b] and determining the presence or concentration of haemoglobin in a stool sample obtained from the subject, and b) wherein the overexpression of at least one of the combinations of miRNAs as compared with the reference expression level measured in healthy control subjects and wherein the presence or higher concentration of haemoglobin as compared with healthy control subjects is indicative that the subject is suffering from colorectal cancer and/or a pre-cancerous stage thereof.

In a preferred embodiment, the pre-cancerous stage of colorectal cancer is advanced colorectal adenoma.

In a preferred embodiment, the diagnosis of the colorectal cancer and/or a pre-cancerous stage thereof is confirmed by an image technique, preferably colonoscopy.

In an embodiment of the first aspect of the invention, optionally in combination with any of the embodiments provided above or below, the method of the invention is performed by using any algorithm known by the expert, for example the algorithms explained in Friedman J H, "Stochastic gradient boosting" Comput Stat Data Anal 2002 38:367-378; for example, by the gradient boosting machine algorithm, C-tree, random forest, linear discrimination analysis, support vector machine, k-nearest neighbor algorithm or logistic regression.

In an embodiment of the first aspect of the invention, optionally in combination with any of the embodiments provided above or below, the method for diagnosing or screening is performed by the gradient boosting machine algorithm.

In an embodiment of the first aspect of the invention, optionally in combination with any of the embodiments provided above or below, the in vitro method for the diagnosis or screening colorectal cancer and/or a pre-cancerous stage thereof which comprises: a) Measuring the expression level of at least miR-421 and/or miR-130b and/or miR-27a, in a biological sample obtained from the subject, in an example the biological sample is a stool sample, and b) wherein the overexpression of miR-421 and/or miR-130b and/or miR-27a, as compared with the reference expression level measured in healthy control subjects, is indicative that the subject is suffering from colorectal cancer and/or a pre-cancerous stage thereof; wherein, optionally, in addition the method comprises the determination of the age and gender of the subject; and wherein the method is performed by an algorithm selected from the following group: gradient boosting machine algorithm, C-tree, random forest, linear discrimination analysis, support vector machine, k-nearest neighbor algorithm and logistic regression.

In an embodiment of the first aspect of the invention, optionally in combination with any of the embodiments provided above or below, the in vitro method for the diagnosis or screening colorectal cancer and/or a pre-cancerous stage thereof which comprises: a) Measuring the expression level of at least miR-421 in a biological sample obtained from the subject, in an example the biological sample is a stool sample, and b) wherein the overexpression of miR-421 as compared with the reference expression level measured in healthy control subjects, is indicative that the subject is suffering from colorectal cancer and/or a pre-cancerous stage thereof; wherein, in addition the method comprises the determination of the age and gender of the subject; and wherein the method is performed by the gradient boosting machine algorithm. This embodiment can optionally comprise in step a) further determining the presence or concentration of haemoglobin in a stool sample obtained from the subject and in step b) in addition, the presence or higher concentration of haemoglobin as compared with healthy control subjects is indicative that the subject is suffering from colorectal cancer and/or a pre-cancerous stage thereof.

In an embodiment of the first aspect of the invention, optionally in combination with any of the embodiments provided above or below, the method comprises: a) measuring the expression level of at least the combination [miR-421 and miR-27a], [miR-421 and miR-25], [miR-421 and miR-221], [miR-421 and miR-34a], [miR-421 and miR-29a] or [miR-421 and miR-130b], and b) wherein the overexpression of at least one of the combinations of miRNAs as compared with the reference expression level measured in healthy control subjects is indicative that the subject is suffering from colorectal cancer and/or a pre-cancerous stage thereof; an wherein in addition the method comprises the determination the age and gender of the subject; and wherein the method is performed by the gradient boosting machine algorithm. This embodiment can optionally comprise in step a) further determining the presence or concentration of haemoglobin in a stool sample obtained from the subject and in step b) in addition, the presence or higher concentration of haemoglobin as compared with healthy control subjects is indicative that the subject is suffering from colorectal cancer and/or a pre-cancerous stage thereof.

The second embodiment of the present invention refers to the in vitro use of at least miR-421 and/or miR-130b and/or miR-27a for screening or diagnosis colorectal cancer and/or a pre-cancerous stage thereof.

In a preferred embodiment, the present invention refers to in vitro use of at least [miR-421 and miR-27a], [miR-421 and miR-25], [miR-421 and miR-221], [miR-421 and miR-34a], [miR-421 and miR-29a], [miR-421 and miR-130b], [miR-130b and miR-27a], [miR-130b and miR-25], [miR-130b and miR-221], [miR-130b and miR-34a] or [miR-130b and miR-29a] for screening or diagnosis colorectal cancer and/or a pre-cancerous stage thereof.

In a preferred embodiment, the present invention refers to in vitro use of at least [miR-130b and miR-27a], [miR-130b and miR-25], [miR-130b and miR-221], [miR-130b and miR-34a] or [miR-130b and miR-29a] for screening or diagnosis colorectal cancer and/or a pre-cancerous stage thereof.

In an embodiment of the second aspect of the invention, optionally in combination with any of the embodiments provided above or below, the in vitro use is performed in a stool, blood, serum or plasma sample.

In an embodiment of the second aspect of the invention, optionally in combination with any of the embodiments provided above or below, the in vitro use is performed in a stool sample.

In a preferred embodiment, the present invention refers to in vitro use of at least the above cited miRNAs in combination with the determination the age and gender of the subject and/or the determination of the presence or concentration of haemoglobin. The third embodiment of the present invention refers to a kit comprising:

Means or reagents for the determination of the presence or concentration of haemoglobin; and Means or reagents for the determination of the expression level of miR-421 and/or miR-130b and/or miR-27a.

In a preferred embodiment the kit comprises:

Means or reagents for the determination of the presence or concentration of haemoglobin; and Means or reagents for the determination of the expression level of [miR-421 and miR-27a], [miR-421 and miR-25], [miR-421 and miR-221], [miR-421 and miR-34a], [miR-421 and miR-29a], [miR-421 and miR-130b], [miR-130b and miR-27a], [miR-130b and miR-25], [miR-130b and miR-221], [miR-130b and miR-34a] or [miR-130b and miR-29a].

In a preferred embodiment the kit comprises:

Means or reagents for the determination of the presence or concentration of haemoglobin; and Means or reagents for the determination of the expression level of [miR-130b and miR-27a], [miR-130b and miR-25], [miR-130b and miR-221], [miR-130b and miR-34a] or [miR-130b and miR-29a].

In a preferred embodiment, the determination of the presence or concentration of haemoglobin is carried out by using antibodies specific to human haemoglobin and the determination of the expression level of miRNAs is carried out by PCR.

In an embodiment of the third aspect of the invention, optionally in combination with any of the embodiments provided above or below, the means or reagents for the determination of the expression level of any of the miRNAs are for reverse transcription quantitative polymerase chain reaction (qRT-PCR).

The fourth embodiment of the present invention refers to the use of the above cited kit for screening or diagnosis colorectal cancer and/or a pre-cancerous stage thereof.

In an embodiment of the fourth aspect of the invention, optionally in combination with any of the embodiments provided above or below, the use is in a stool sample of a subject.

According to the method of the invention, after measuring the expression level of any of the above cited combinations of biomarkers, a score value is obtained for the signature and this score value is compared with a threshold value which defines the diagnostic rule. If this score value is higher than the threshold, then the corresponding sample is classified as a positive sample, which is an indication that the patient might be suffering from colorectal cancer and/or pre-cancerous stage thereof. The threshold value has been defined in order to optimize sensitivity and specificity values. Consequently, in a preferred embodiment, the method of the invention comprises: a) Measuring the concentration level of any of the above cited combinations of biomarkers, in a biological sample obtained from the subject, b) processing the expression values in order to obtain a risk score and c) wherein if a deviation or variation of the risk score value obtained for any of the above cited combinations of biomarkers is identified, as compared with a reference value, this is indicative that the subject is suffering from colorectal cancer and/or a pre-cancerous stage.

All the embodiments of the first aspect of the invention are also embodiments of the second, third and fourth aspect of the invention.

In an embodiment of the first, second, third or fourth aspect of the invention, optionally in combination with any of the embodiments provided above or below, the miRNAs expression level is measured by qRT-PCR.

The last embodiment of the present invention refers to a method for treating colorectal cancer or a pre-cancerous stage thereof, which comprises: a) diagnosing a patient with colorectal cancer or a pre-cancerous stage thereof according to any of the above described embodiments and b) treating the patient by performing a colonoscopy which might include removing colorectal cancer lesions or polyps. This method for treating colorectal cancer or a pre-cancerous stage thereof is named hereinafter as the "method of treatment of the present invention".

All the embodiments of the first, second, third and fourth aspects of the invention are also embodiments of the method of treatment of the present invention.

In an embodiment of the method of treatment of the present invention, optionally in combination with any of the embodiments provided above or below, in step b) patients in whom colorectal cancer was diagnosed will be treated by endoscopic polypectomy, surgical resection, chemotherapy (for example, fluoropyrimidines, oxiplatin and/or irinotecan) and/or radiotherapy, for example, depending on the tumor stage; whereas in patients in whom advanced adenomas are diagnosed will be treated by endoscopic polypectomy or surgical resection, for example, depending on polyp size.

For the purpose of the present invention the following terms are defined:

The term "colorectal cancer" is a medical condition characterized by cancer of cells of the intestinal tract below the small intestine (i.e., the large intestine (colon), including the cecum, ascending colon, transverse colon, descending colon, sigmoid colon, and rectum).

The expression "colorectal adenoma" refers to adenomas of the colon, also called adenomatous polyps, which is a benign and pre-cancerous stage of the colorectal cancer but still with high risk of progression to colorectal cancer.

The expression "advanced colorectal adenoma" refers to adenomas having a size of at least 10 mm or histologically having high grade dysplasia or a villous component higher than 20%.

The expression "non-invasive biological sample" refers to any sample which is taken from the body of the patient without the need of using harmful instruments, other than fine needles used for taking the blood from the patient, and consequently without being harmfully for the patient. Specifically, non-invasive biological sample refers in the present invention to: stool, blood, serum, or plasma samples.

The expression "reference expression level measured in healthy control subjects" refers to a "reference value" of the expression level of the biomarkers. If a deviation of the expression level of the biomarkers is determined with respect to said "reference expression level measured in healthy control subjects", this is an indication of colorectal cancer or pre-cancerous stage thereof. Particularly, if the expression level of the biomarkers or signatures of the present invention are significantly higher or lower with respect to said "reference value" this is an indication of colorectal cancer or pre-cancerous stage thereof.

The expression "risk score" refers to a risk value obtained after processing one or more concentration values into a single value (or risk value), which represents the probability of disease for the individual. This risk value will be compared with a reference value to evaluate if the patient might be suffering from colorectal cancer and/or pre-cancerous stage thereof.

A "reference value" can be a threshold value or a cut-off value. Typically, a "threshold value" or "cut-off value" can be determined experimentally, empirically, or theoretically. A threshold value can also be arbitrarily selected based upon the existing experimental and/or clinical conditions, as would be recognized by a person of ordinary skilled in the art. The threshold value has to be determined in order to obtain the optimal sensitivity and specificity according to the function of the test and the benefit/risk balance (clinical consequences of false positive and false negative). Preferably, the person skilled in the art may compare the biomarker levels (or scores) obtained according to the method of the invention with a defined threshold value. Typically, the optimal sensitivity and specificity (and so the threshold value) can be determined using a Receiver Operating Characteristic (ROC) curve based on experimental data. For example, after determining the levels of the biomarkers in a group of reference, one can use algorithmic analysis for the statistic treatment of the measured concentrations of biomarkers in biological samples to be tested, and thus obtain a classification standard having significance for sample classification. The full name of ROC curve is receiver operator characteristic curve, which is also known as receiver operation characteristic curve. It is mainly used for clinical biochemical diagnostic tests. ROC curve is a comprehensive indicator that reflects the continuous variables of true positive rate (sensitivity) and false positive rate (1-specificity). It reveals the relationship between sensitivity and specificity with the image composition method. A series of different cut-off values (thresholds or critical values, boundary values between normal and abnormal results of diagnostic test) are set as continuous variables to calculate a series of sensitivity and specificity values. Then sensitivity is used as the vertical coordinate and specificity is used as the horizontal coordinate to draw a curve. The higher the area under the curve (AUC), the higher the accuracy of diagnosis. On the ROC curve, the point closest to the far upper left of the coordinate diagram is a critical point having both high sensitivity and high specificity values. The AUC value of the ROC curve is between 1.0 and 0.5. When AUC>0.5, the diagnostic result gets better and better as AUC approaches 1. Existing software or systems in the art may be used for the drawing of the ROC curve, such as: MedCalc 9.2.0.1 medical statistical software, SPSS 9.0 or pROC R package.

By "comprising" it is meant including, but not limited to, whatever follows the word "comprising". Thus, use of the term "comprising" indicates that the listed elements are required or mandatory, but that other elements are optional and may or may not be present.

By "consisting" of it is meant "including, and limited to", whatever follows the phrase "consisting of". Thus, the phrase "consisting of" indicates that the listed elements are required or mandatory, and that no other elements may be present.

Throughout the description and claims the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

DETAILED DESCRIPTION OF THE INVENTION

Example 1. Material and Methods

Example 1.1 Patients and Methods

Figure 1:
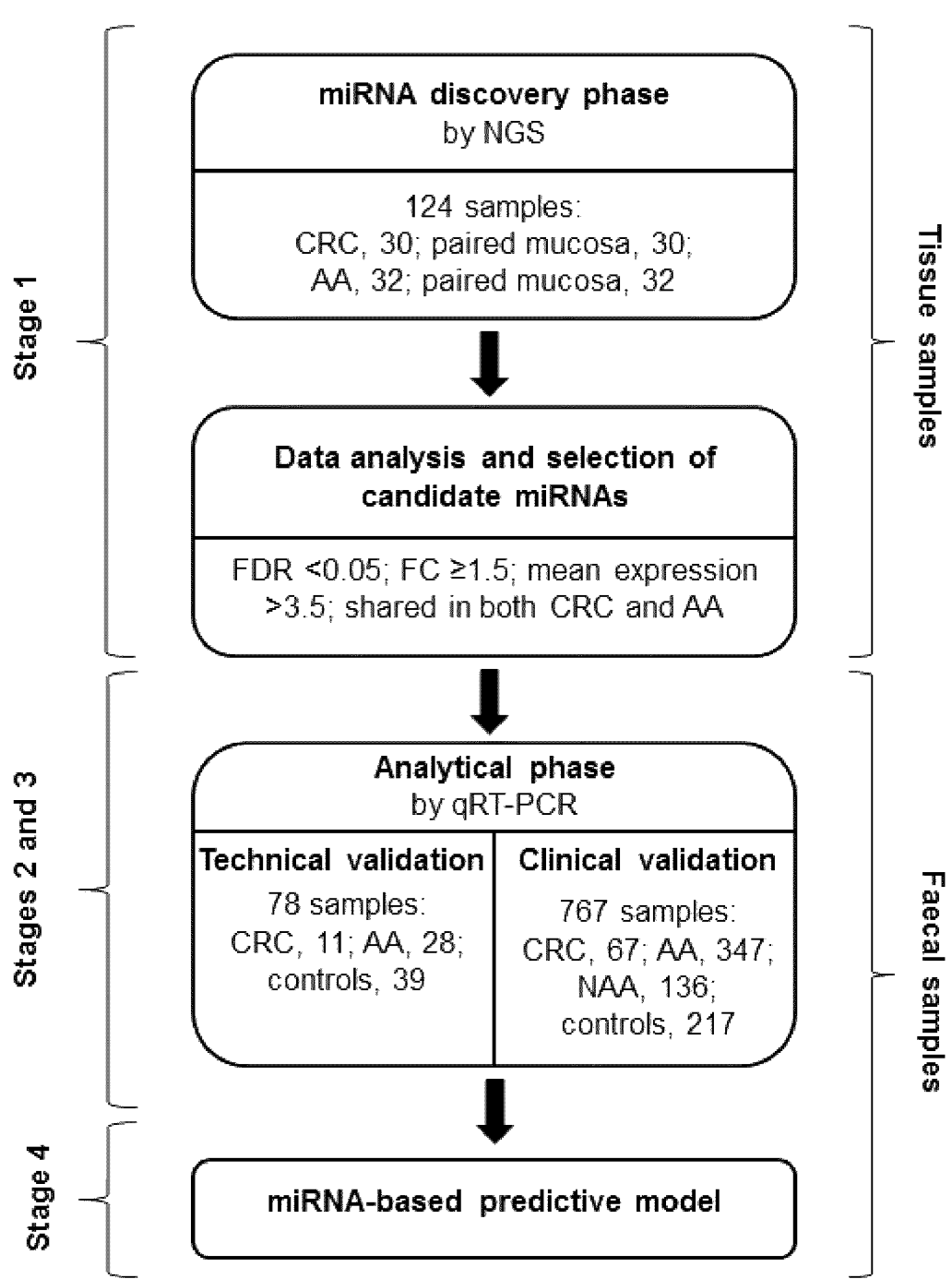
FIG. 1. Outline of the study. CRC, colorectal cancer; AA, advanced adenomas; NAA, non-advanced adenomas; FDR, false discovery rate; FC, fold change.

The study comprised four main stages: 1) miRNA discovery phase by next generation sequencing (NGS) in a tissue set of CRC and AA samples, along with their paired normal mucosa; 2) technical validation of miRNA candidates by quantitative reverse-transcription PCR (qRT-PCR)

in faecal samples from a subset of patients included in the discovery phase as well as control individuals; 3) clinical validation of the most significantly up-regulated miRNAs by qRT-PCR in an independent set of faecal samples obtained from participants in the Barcelona's CRC screening program; and 4) development of a miRNA-based predictive model to discriminate patients with advanced neoplasm (i.e. CRC or AA) of those with non-relevant findings at colonoscopy. The outline of study is shown in FIG. 1.

For the miRNA discovery phase, 124 fresh colorectal tissue samples were prospectively collected at the Hospital Clinic of Barcelona. Paired neoplastic and normal mucosa samples were obtained from 30 patients with CRC submitted to surgery; none of these patients had received either neo-adjuvant chemotherapy or radiation therapy. In addition, paired neoplastic and normal mucosa samples were obtained from 32 patients with AA after endoscopic resection. All tissue samples were preserved in RNAlater® (Invitrogen, Carlsbad, CA) and frozen at −80° C. until RNA extraction.

For the technical validation of miRNA candidates in faecal samples, a subset of 39 patients included in the previous stage (11 with CRC and 28 with AA) and 39 control individuals with normal colonoscopy were analyzed.

Finally, clinical validation of selected miRNA was performed in 767 faecal samples recruited among FIT-positive participants in the Barcelona's CRC screening program between March 2011 and May 2017. Each participant provided one faecal sample using a specimen collection device (OC-Sensor, Eiken Chemical Co., Japan), which collects 10 mg faeces with a serrated probe attached to the cap into 2 mL buffer. All samples were kept at −80° C. until RNA extraction. Characteristics of the population-based, organized screening program are described elsewhere.

Clinic-pathological features of all individuals included in the study are shown in Table 3. The study was approved by the Institutional Ethics Committee of Hospital Clinic of Barcelona, and written informed consent was obtained from all participants in accordance with the Declaration of Helsinki.

Example 1.2. MicroRNA Extraction

Total RNA, including miRNAs, was isolated from tissues or faeces (500 μL buffer) using the miRNeasy® mini kit (Qiagen, Valencia, CA) according to the manufacturer's protocol. For tissue samples, after the RNA extraction, an RNeasy MinElute Cleanup® kit (Qiagen, Valencia, CA) was used to warrant removal of contaminants and to concentrate samples in a final elution volume of 12 μL. The purity of RNA tissue samples was analysed using Agilent 2100 Bioanalyzer (Agilent Technologies, Palo Alto, CA) and concentration was determined by NanoDrop® 1000 spectrophotometer (Wilmington, DE). Concentration of total miRNA present in faecal samples was measured by Quant-iT® microRNA assay kit (Invitrogen, Carlsbad, CA).

Example 1.3. Genome-Wide miRNA Profiling by NGS

Generation of small RNA libraries was performed from 1 μg of total RNA from tissue using TruSeq® small RNA sample prep kit (Illumina, San Diego, CA) according to the manufacturer's protocol. First, 3' and 5' RNA adapters were ligated at the small RNA ends. Thereafter, cDNA constructs were synthetized by reverse transcription using Super-Script® II reverse transcriptase (Invitrogen, Carlsbad, CA) with specific primers complementary to the 3'RNA adapter.

cDNA was further amplified by PCR using indexed adapters supplied in the kit. This step selectively enriches RNA fragments with adapter molecules in both ends. Finally, the amplified cDNA constructs from libraries were isolated on a 6% Novex® TBE gels (Life Technologies, Carlsbad, CA). The area representing the band size of 18 to 36 base pairs (bp) was cut from the gel, and DNA was precipitated and eluted in 10 μL of elution buffer. The cDNA libraries generated were analyzed using Agilent High Sensitivity DNA® kit (Agilent Technologies, CA) to ensure acceptable quantity and check size distribution. The high-throughput sequencing of the cDNA libraries was run in HiSeq® 2000 (Illumina, CA) with 1×50 bp single-end reads to obtain >15M reads per sample. Quality control was made by image analysis and assignation of bases by Real Time Analysis software. We discarded reads with low confidence values in the first 25 bases. Quality control reads were aligned with a reference genome with GEM program. The error percentage was below 2.5% calculated from a Genome of PhiX added to the samples before sequencing.

Example 1.4. Analysis of Faecal miRNA Expression by qRT-PCR qRT-PCR was done using singleplex TaqMan® microRNA assays (Applied Biosystems Inc., Foster City, CA). Briefly, 5 ng of total miRNA were used to perform retro-transcription. Thereafter, a pre-amplification step was performed in some miRNAs before quantitative qPCR due to the low miRNA levels in faeces. Finally, qPCR was performed in a Viia7® Real Time PCR system (Applied Biosystems Inc., Foster City, CA) using 2 μL of cDNA in a final volume of 10 μL. Each point was assessed in triplicate.

Due to the lack of a reliable endogenous control to normalize faecal miRNAs, absolute quantification was carried out. Thus, the average Ct for each sample was converted to ng of specific miRNA/g of total miRNA using standard curves made by serial dilutions of known quantities of each specific synthetic miRNA (Integrated DNA Technologies, IA).

Example 1.5. Bioinformatics and Statistical Analysis

Sequencing analysis was done by using the sRNAbench package. Briefly, after adapter trimming and unique read grouping, reads were aligned to the human genome (UCSC hg19) using Bowtie 1.1.2 allowing for one mismatch. To provide annotations for RNA elements that mapped to the human genome, miRBase (version 21) for mature and pre-miRNA sequences was used. Count data were voom-transformed to log 2-counts per million (logCPM) and normalized by cyclic-loess method. To identify differentially expressed miRNAs, moderated-t statistics were applied. Differential expression, fold change and expression mean as log 2 of the difference were analyzed between colorectal neoplastic tissue and paired normal mucosa. P-values were adjusted for multiple testing by Benjamini and Hochberg method. MiRNAs with false discovery rate <0.05 were considered significant. Principal component analysis plots were made to visualize high dimensional data in a 2D graph in which the areas delimited by the ellipses represents 95% of the binomial distribution of the sample scores on the first and second axes. Venn diagrams considering significant miRNAs were also performed. Selection of miRNA candidates from NGS results was made based on the following criteria: false discovery rate <0.05, fold change ≥1.5, mean expression >3.5, and up-regulation in both CRC and AA.

For quantitative variables, Student's t test was used. Discriminative capacity of individual miRNAs was evaluated by multivariate logistic regression, adjusted by age and gender. P-value ≤0.05 was regarded as significant. Area under the receiver operating characteristics (AUC) curve and the derived cut-points were computed using pROC R-package considering each miRNA as a continuous variable. Sensitivity and specificity were calculated from the optimal cut-point associated with the minimum error rate.

Example 1.6. Faecal miRNA-Based Predictive Modelling

The predictive model to discriminate between different groups of individuals was performed considering miRNAs results obtained in the clinical validation phase, along with age and gender. Primary endpoint of this analysis was to discriminate patients with advanced neoplasm (i.e. CRC or AA) of those with non-relevant findings at colonoscopy (i.e. NAA or normal examination). Secondary endpoints were to distinguish patients with advanced neoplasm, CRC and AA from individuals with normal colonoscopy, respectively.

For predictive model generation, samples were randomly split into training and test sets as 75%-25% proportion. Then, numeric data were pre-processed by centering and scaling. To address the imbalance of sample groups, synthetic minority over-sampling technique was used. In the training set, a 10-fold cross-validation was performed. Algorithms tested for the generation of the model were: C-tree, random forest, linear discriminant analysis, gradient boosting machine, support vector machine, and K-nearest neighbor. P-value <0.05 was regarded as significant. Discrimination measures were AUC, sensitivity, specificity, and positive and negative predicted values. A post-processing calibration was made with 15 predicted versus observed probability bins in order to analyze the error distribution of the predictive model. All analyses were performed with R under CARET package.

Results obtained with the faecal miRNA-based predictive model were compared to the one that would be achieved by using faecal haemoglobin concentration, adjusted by age and gender, which represents the standard of care in most CRC screening program.

Finally, performance of a predictive model combining both miRNA signature and faecal haemoglobin concentration was also assessed.

Example 2. Results

Example 2.1. MiRNA Discovery Phase by NGS

Figure 2:
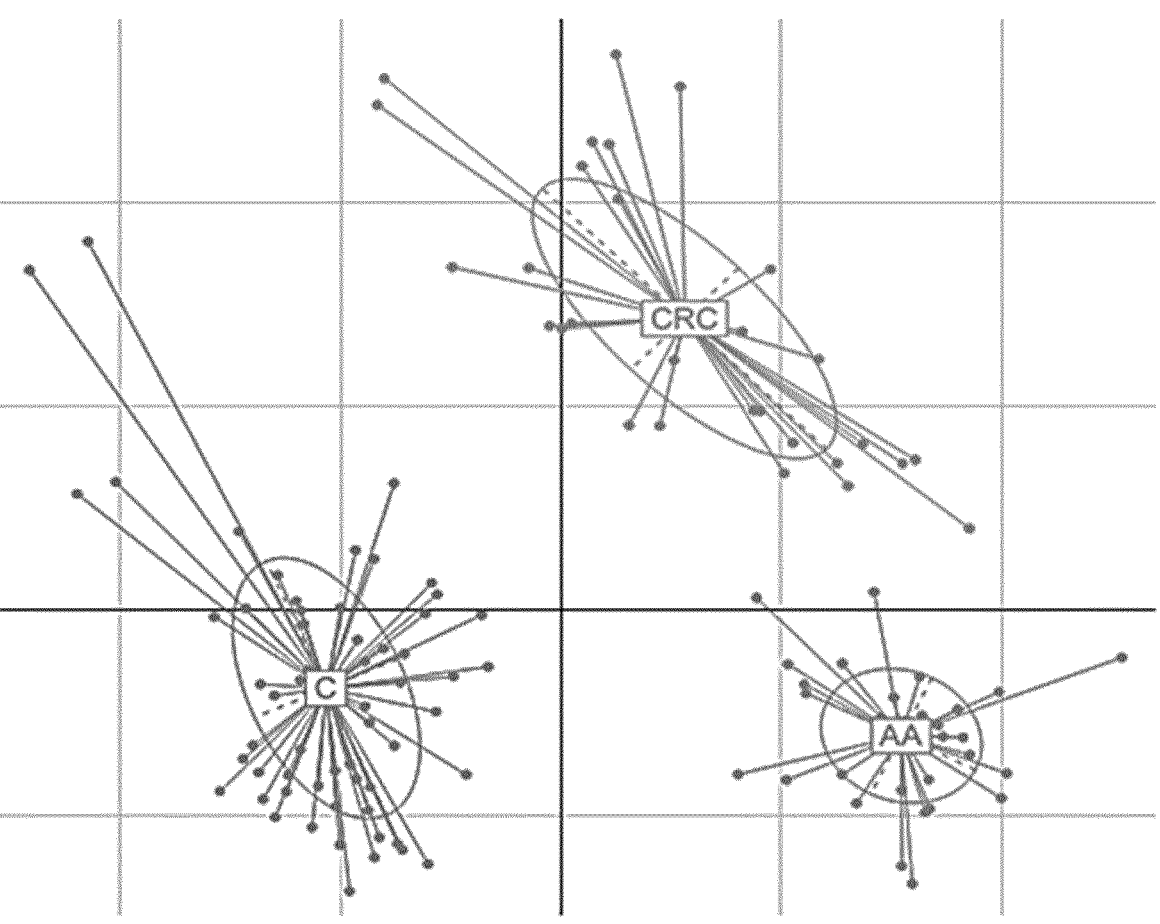
FIG. 2. Panel A. Between-group analysis plot depicting sample clustering based on miRNA expression profile. CRC, colorectal cancer; AA, advanced adenoma; C, paired normal tissue. Panel B. Venn diagram generated from NGS results of 124 tissue samples. Inside circles, miRNAs with false discovery rate <0.05 and fold change ≥1.5 or ≥−1.5 are shown. Convergence between circles is the common significant deregulated miRNAs in both neoplastic lesions. Red, number of up-regulated miRNAs; green, number of down-regulated miRNAs.
Figure 2:
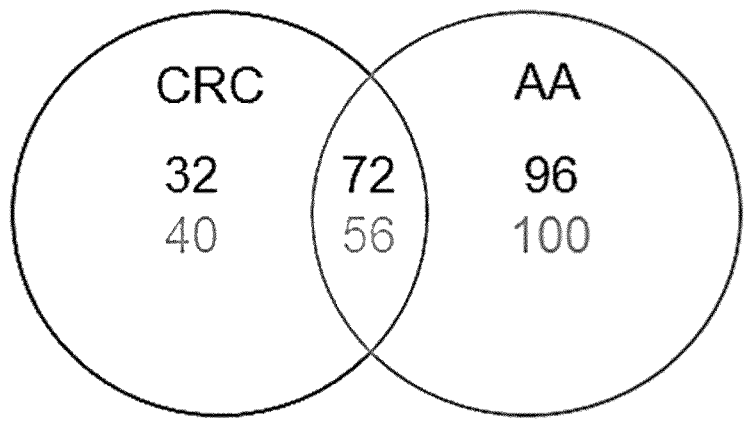

In the tissue set of colorectal samples, expression of 1640 miRNAs was detected and 637 miRNAs had more than 100 counts. Of them, 200 and 324 miRNAs were significantly deregulated in CRC and AA, respectively, in comparison to their paired normal mucosa, with a fold change ≥1.5. Between-group analysis showed that miRNA expression profiling could distinguish CRC or AA tissue samples from their paired normal mucosa (FIG. 2A), as well CRC from AA. Moreover, we found that 72 and 56 miRNAs were commonly up- or down-regulated, respectively, in both neoplastic lesions (FIG. 2B).

According to the selection criteria (i.e. false discovery rate <0.05, fold change ≥1.5, mean expression >3.5, and up-regulation in both CRC and AA), 21 miRNA candidates (Table 4) were selected for technical validation in faecal samples.

Example 2.2. MiRNA Analysis on Faecal Samples by qRT-PCR

In order to elucidate whether miRNA patterns in colorectal tissues could be reproduced in faecal samples, we first analyzed by qRT-PCR the above-mentioned 21 miRNAs in a subset of 39 patients included in the discovery phase (11 patients with CRC and 28 with AA) as well as 39 control individuals with normal colonoscopy.

Results of this technical validation phase showed that 7 miRNAs were significantly up-regulated in faecal samples from patients with CRC (miR-130b-3p, miR-21-5p, miR-221-5p, miR-25-3p, miR-27a-3p, miR-34a-5p, and miR-421). In addition, four of them (miR-130b-3p, miR-21-5p, miR-27a-3p and miR-421) as well as miR-335-3p were significantly up-regulated in faecal samples from patients with AA. These 8 miRNAs, along with miR-29a-3p, which was also up-regulated in faecal samples from patients with CRC and AA (AUC of 0.84 and 0.71, respectively; p-value <0.1), were selected to be clinically validated in an independent cohort of participants in the CRC screening program.

Example 2.3. Clinical Validation of miRNA Candidates

The above-mentioned 9 up-regulated miRNAs were validated in faecal samples from a prospectively collected cohort of 767 FIT-positive individuals, which included 67 patients with CRC, 347 patients with AA, 136 patients with NAA, and 217 individuals with normal colonoscopy (Table 3).

In this set of samples, up-regulation of miR-25-3p, miR-27a-3p, miR-29a-3p, miR-34a-5p, miR-130b-3p, miR-221-3p, and miR-421 was confirmed in CRC patients (AUCs ranging from 0.69 to 0.77), whereas up-regulation of miR-130b-3p and miR-421 was confirmed in patients with AA (AUCs were 0.69 and 0.71, respectively), in comparison with the control group. It is important to note that none of these 7 faecal miRNAs showed significant differences between patients with NAA and individuals with normal colonoscopy (Table 5).

Finally, with respect to the primary endpoint of study, miR-421, miR-27a-3p and miR-130b-3p were significantly selected as the most discriminant faecal miRNAs to distinguish patients with advanced neoplasm from those with non-relevant findings at colonoscopy (Table 6).

Development and Validation of a Faecal miRNA-Based Predictive Model for Colorectal Cancer Screening Predictive modelling to discriminate between different groups of patients was performed considering faecal miRNAs significantly up-regulated in patients with advanced neoplasm, along with age and gender. According to the principal component analysis miR-421 and miR-27a were finally selected for this purpose because they were shown not to be redundant among the three most discriminant faecal miRNAs. For model generation, individuals were randomly split into training (n=578) and test sets (n=189), with a 10-fold cross-validation in the development stage to reduce bias and variability. As previously mentioned, different algorithms were tested in order to choose the one that fitted better with respect to the primary endpoint of the study, being the gradient boosting machine (GBM) algorithm finally selected based on its highest accuracy.

As it is shown in Table 7, the resulting predictive model combining miR-421, miR-27a, age and gender was highly accurate (AUC=0.63) to identify patients with advanced neoplasm among FIT-positive participants in the CRC screening program. Interestingly, this result was due not only to a high accuracy for recognizing patients with CRC (AUC=0.74; sensitivity, 96%), but also to distinguishing patients with AA from control individuals (AUC=0.64; sensitivity, 59%).

The results achieved in the faecal miRNA-based predictive model [miR-421 and miR-27a] were superior to those obtained using faecal haemoglobin concentration as classifier, with respect to detection of advanced neoplasm (AUC=0.62 when compared with subjects with non-relevant findings at colonoscopy; AUC=0.59 when compared with individuals with normal colonoscopy), CRC (AUC=0.67) and AA (AUC=0.59) (Table 7).

Figure 3:
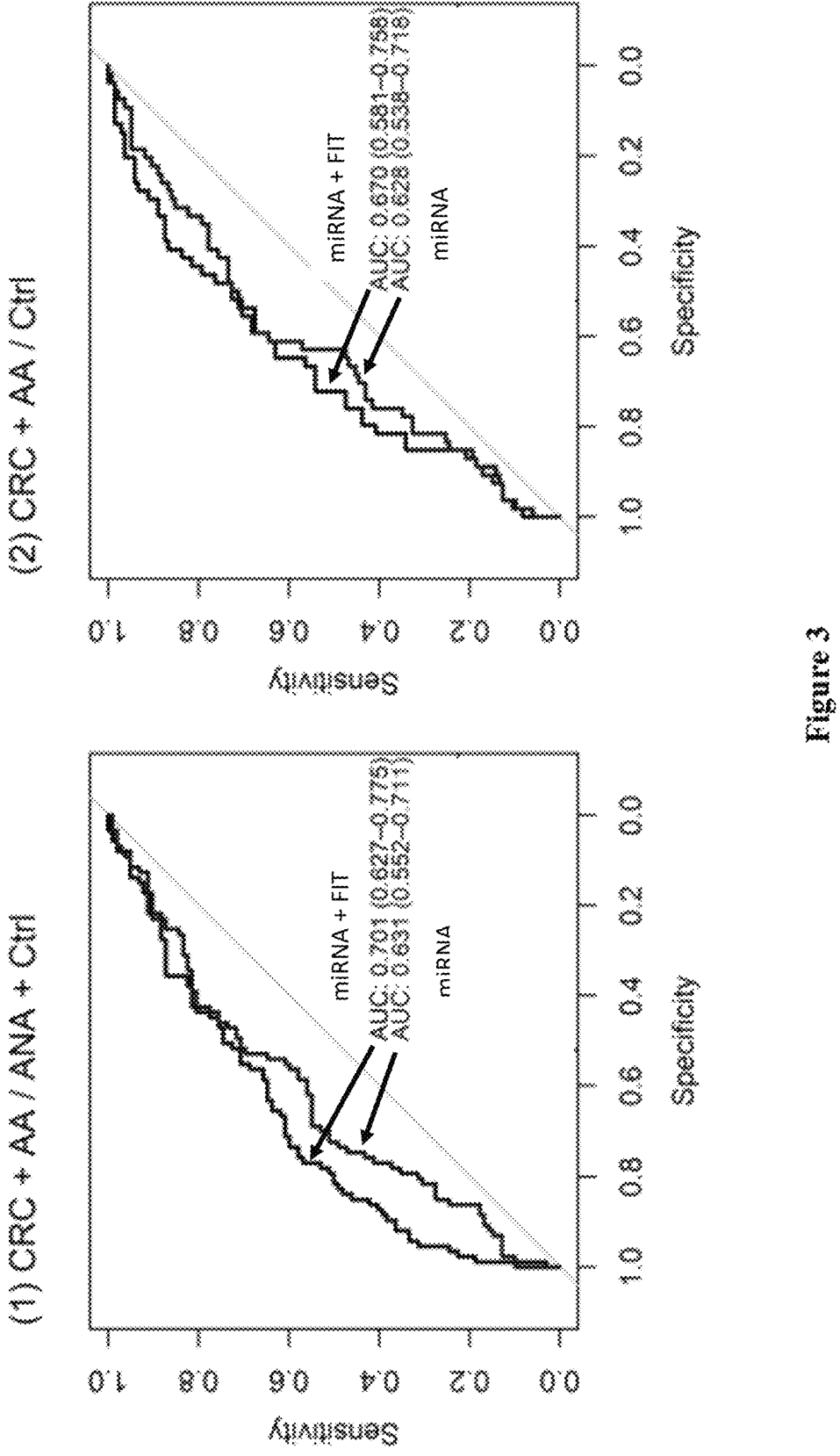
FIG. 3. Receiver-operating-characteristic (ROC) curves of the best miRNA-faecal predictive model (miR-421, miR-27a, age, gender) as calculated by GBM algorithm, present high capacity to distinguish: 1) advanced colorectal neoplasia (CRC+AA) vs non-advanced colorectal neoplasia (NAA+healthy control) 2) advanced colorectal neoplasia (CRC+AA) vs healthy control 3) CRC vs healthy control and, 4) AA vs healthy control. Area Under Curve (AUC). X axis represents Specificity. Y axis represents Sensitivity.

Finally, such as it can be seen in FIG. 3, the combination of both miRNA signature [miR-421 and miR-27a] and faecal haemoglobin concentration allowed the highest accuracy for identifying patients with advanced neoplasm (AUC=0.70 when compared with subjects with non-relevant findings at colonoscopy; AUC=0.67 when compared with individuals with normal colonoscopy), CRC (AUC=0.93) and AA (AUC=0.64) (Table 7). Indeed, calibration curves of the combined model indicated that predictions were closer to the observed outcomes, and the error distribution was lower, in comparison to the results obtained using faecal haemoglobin concentration alone.

TABLE 1

| | CRC | | Adenoma | | Advanced Colorectal neoplasia | |
|---|---|---|---|---|---|---|
| Signatue | AUC | [CI] | AUC | [CI] | AUC | [CI] |
| miR-421 | 0.74 | [0.67-0.81] | 0.68 | [0.64-0.72] | 0.69 | [0.65-0.73] |
| miR-421 + miR-27a | 0.73 | [0.66-0.80] | 0.68 | [0.63-0.72] | 0.69 | [0.64-0.73] |
| miR-421 + miR-25 | 0.76 | [0.69-0.83] | 0.68 | [0.64-0.73] | 0.69 | [0.65-0.73] |
| miR-421 + miR-221 | 0.74 | [0.67-0.81] | 0.68 | [0.64-0.73] | 0.69 | [0.65-0.73] |
| miR-421 + miR-34a | 0.73 | [0.66-0.81] | 0.68 | [0.63-0.73] | 0.69 | [0.65-0.73] |
| miR-421 + miR-29a | 0.73 | [0.66-0.80] | 0.68 | [0.64-0.73] | 0.69 | [0.64-0.73] |
| miR-421 + miR-130b | 0.72 | [0.65-0.80] | 0.68 | [0.63-0.72] | 0.69 | [0.64-0.73] |
| miR-421 + age + gender | 0.77 | [0.70-0.84] | 0.71 | [0.67-0.75] | 0.72 | [0.68-0.76] |
| miR-421 + miR-27a + age + gender | 0.78 | [0.71-0.85] | 0.71 | [0.67-0.75] | 0.72 | [0.68-0.76] |
| miR-421 + miR-25 + age + gender | 0.79 | [0.72-0.85] | 0.71 | [0.67-0.76] | 0.72 | [0.68-0.76] |
| miR-421 + miR-221 + age + gender | 0.79 | [0.72-0.85] | 0.71 | [0.67-0.76] | 0.72 | [0.68-0.76] |
| miR-421 + miR-34a + age + gender | 0.78 | [0.71-0.85] | 0.71 | [0.67-0.76] | 0.72 | [0.68-0.76] |
| miR-421 + miR-29a + age + gender | 0.78 | [0.71-0.84] | 0.71 | [0.67-0.76] | 0.72 | [0.68-0.76] |

TABLE 1-continued

| Signatue | CRC AUC | [CI] | Adenoma AUC | [CI] | Advanced Colorectal neoplasia AUC | [CI] |
|---|---|---|---|---|---|---|
| miR-421 + miR-130b + age + gender | 0.77 | [0.70-0.84] | 0.71 | [0.67-0.76] | 0.72 | [0.68-0.76] |
| miR-421 + age + gender + Hg | 0.81 | [0.75-0.87] | 0.71 | [0.67-0.75] | 0.72 | [0.68-0.77] |
| miR-421 + miR-27a + age + gender + Hg | 0.81 | [0.76-0.87] | 0.71 | [0.67-0.75] | 0.72 | [0.68-0.77] |
| miR-421 + miR-25 + age + gender + Hg | 0.81 | [0.76-0.87] | 0.71 | [0.67-0.76] | 0.73 | [0.68-0.77] |
| miR-421 + miR-221 + age + gender + Hg | 0.82 | [0.76-0.88] | 0.71 | [0.67-0.75] | 0.72 | [0.68-0.77] |
| miR-421 + miR-34a + age + gender + Hg | 0.81 | [0.75-0.87] | 0.71 | [0.67-0.75] | 0.72 | [0.68-0.77] |
| miR-421 + miR-29a + age + gender + Hg | 0.81 | [0.75-0.87] | 0.71 | [0.67-0.76] | 0.72 | [0.68-0.77] |
| miR-421 + miR-130b + age + gender + Hg | 0.80 | [0.74-0.86] | 0.71 | [0.67-0.76] | 0.73 | [0.68-0.77] |

TABLE 1

| Signatue | CRC AUC | [CI] | Adenoma AUC | [CI] | Advanced Colorectal neoplasia AUC | [CI] |
|---|---|---|---|---|---|---|
| miR-130b | 0.62 | [0.55-0.70] | 0.62 | [0.57-0.66] | 0.62 | [0.58-0.66] |
| miR-130b + miR-27a | 0.62 | [0.54-0.71] | 0.62 | [0.57-0.67] | 0.62 | [0.57-0.67] |
| miR-130b + miR-25 | 0.66 | [0.58-0.74] | 0.63 | [0.58-0.67] | 0.62 | [0.58-0.67] |
| miR-130b + miR-221 | 0.63 | [0.55-0.71] | 0.63 | [0.58-0.68] | 0.62 | [0.58-0.67] |
| miR-130b + miR-34a | 0.65 | [0.57-0.73] | 0.62 | [0.58-0.67] | 0.62 | [0.57-0.66] |
| miR-130b + miR-29a | 0.61 | [0.53-0.69] | 0.63 | [0.58-0.68] | 0.62 | [0.57-0.67] |
| miR-130b + age + gender | 0.71 | [0.63-0.78] | 0.69 | [0.64-0.73] | 0.69 | [0.64-0.73] |
| miR-130b + miR-27a + age + gender | 0.71 | [0.64-0.79] | 0.69 | [0.64-0.74] | 0.69 | [0.64-0.73] |
| miR-130b + miR-25 + age + gender | 0.72 | [0.65-0.79] | 0.70 | [0.65-0.74] | 0.69 | [0.65-0.73] |
| miR-130b + miR-221 + age + gender | 0.72 | [0.64-0.79] | 0.69 | [0.65-0.74] | 0.69 | [0.64-0.73] |
| miR-130b + miR-34a + age + gender | 0.72 | [0.65-0.79] | 0.69 | [0.64-0.74] | 0.69 | [0.64-0.73] |
| miR-130b + miR-29a + age + gender | 0.71 | [0.64-0.78] | 0.69 | [0.65-0.74] | 0.69 | [0.64-0.73] |
| miR-130b + age + gender + Hg | 0.75 | [0.68-0.81] | 0.69 | [0.64-0.73] | 0.70 | [0.65-0.74] |
| miR-130b + miR-27a + age + gender + Hg | 0.75 | [0.69-0.82] | 0.69 | [0.64-0.73] | 0.69 | [0.65-0.74] |
| miR-130b + miR-25 + age + gender + Hg | 0.76 | [0.69-0.82] | 0.69 | [0.65-0.74] | 0.70 | [0.65-0.74] |
| miR-130b + miR-221 + age + gender + Hg | 0.76 | [0.69-0.82] | 0.69 | [0.64-0.74] | 0.70 | [0.65-0.74] |
| miR-130b + miR-34a +age + gender+ Hg | 0.76 | [0.69-0.82] | 0.69 | [0.64-0.73] | 0.70 | [0.65-0.74] |
| miR-130b + miR-29a + age + gender + Hg | 0.75 | [0.69-0.81] | 0.69 | [0.65-0.74] | 0.69 | [0.65-0.74] |

TABLE 3

| | Discovery phase (n = 124) | | Technical validation phase (n = 78) | | |
|---|---|---|---|---|---|
| | CRC (n = 30) | AA (n = 32) | CRC (n = 11) | AA (n = 28) | Control (n = 39) |
| Age, mean (SD) | 72 (12.2) | 59.6 (5.5) | 68.3 (12.5) | 59 7 (5.4) | 59.2 (6.1) |
| Gender, no. (%) | | | | | |
| Female | 16 (53.3) | 13 (40.6) | 5 (45.5) | 12 (42.9) | 29 (74.4) |
| Male | 14 (46.7) | 19 (59.4) | 6 (54.5) | 16 (57.1) | 10 (25.6) |
| CRC characteristics | | | | | |
| Tumour location, no. (%) | | | | | |
| Proximal | 12 (40.0) | — | 6 (54.5) | — | — |
| Distal | 18 (60.0) | — | 5 (45.5) | — | — |
| Tumour stage, no. (%) | | | | | |
| I | 9 (30.0) | — | 5 (45.5) | — | — |
| II | 12 (40.0) | — | 4 (36.4) | — | — |
| III | 8 (26.7) | — | 2 (18.2) | — | — |
| IV | 1 (3.3) | — | — | — | — |
| Unknown | — | — | — | — | — |

TABLE 3-continued

| AA characteristics (%) | | | | | |
|---|---|---|---|---|---|
| Three or more polyps, no. (%) | — | — | — | 18 (64.3) | — |
| Size ≥10 mm, no. (%) | — | 32 (100.0) | — | 28 (100.0) | — |
| HGD, no. (%) | — | 2 (6.3) | — | 1 (3.6) | — |
| Villous component, no. (%) | — | 6 (18.8) | — | 6 (21.4) | — |
| Carcinoma in situ, no. (%) | — | 1 (3.1) | — | — | — |

| | Clinical validation phase (n = 767) | | | |
|---|---|---|---|---|
| | CRC (n = 67) | AA (n = 347) | NAA (n = 136) | Control (n = 217) |
| Age, mean (SD) | 63 (7.8) | 59.9 (5.9) | 59.8 (5.5) | 59.4 (5.7) |
| Gender, no. (%) | | | | |
| Female | 27 (40.3) | 115 (33.1) | 60 (44.1) | 131 (60.4) |
| Male | 40 (59.7) | 232 (66.9) | 76 (55.9) | 86 (39.6) |
| CRC characteristics | | | | |
| Tumour location, no. (%) | | | | |
| Proximal | 20 (29.9) | — | — | — |
| Distal | 47 (70.1) | — | — | — |
| Tumour stage, no. (%) | | | | |
| I | 23 (34.3) | — | — | — |
| II | 16 (23.9) | — | — | — |
| III | 18 (26.8) | — | — | — |
| IV | 5 (7.5) | — | — | — |
| Unknown | 5 (75) | — | — | — |
| AA characteristics (%) | | | | |
| Three or more polyps, no. (%) | — | 224 (64.5) | — | — |
| Size ≥10 mm, no. (%) | — | 275 (79.3) | — | — |
| HGD, no. (%) | — | 75 (21.6) | — | — |
| Villous component, no. (%) | — | 93 (26.8) | — | — |
| Carcinoma in situ, no. (%) | — | 17 (4.9) | — | — |

TABLE 4

| | Discovery phase (NGS) | | | | |
|---|---|---|---|---|---|
| | CRC vs. normal mucosa | | AA vs. normal mucosa | | Expression |
| MicroRNA | FC | FDR | FC | FDR | mean |
| miR-106b-5p | 1.72 | 3.28E−11 | 1.72 | 3.28E−11 | 5.9 |
| miR-130b-3p | 1.96 | 1.56E−10 | 1.96 | 1.56E−10 | 6.1 |
| miR-17-5p | 2.07 | 1.52E−10 | 2.07 | 1.52E−10 | 8.4 |
| miR-182-5p | 6.32 | 7.56E−20 | 6.32 | 7.56E−20 | 10.4 |
| miR-183-5p | 6.25 | 5.42E−19 | 6.25 | 5.42E−19 | 7.9 |
| miR-18a-3p | 2.00 | 4.82E−08 | 2.00 | 4.82E−08 | 3.8 |
| miR-203a | 2.73 | 4.93E−13 | 2.73 | 4.93E−13 | 7.7 |
| miR-20a-5p | 2.21 | 6.07E−10 | 2.21 | 6.07E−10 | 8.7 |
| miR-21-5p | 1.54 | 1.95E−08 | 1.54 | 1.95E−08 | 12.5 |
| miR-221-3p | 2.11 | 4.80E−14 | 2.11 | 4.80E−14 | 9.4 |
| miR-24-3p | 1.72 | 2.79E−09 | 1.72 | 2.79E−09 | 7.5 |
| miR-25-3p | 1.46 | 1.54E−06 | 1.46 | 1.54E−06 | 11.8 |
| miR-27a-3p | 1.70 | 5.59E−08 | 1.70 | 5.59E−08 | 7.4 |
| miR-29a-3p | 1.89 | 2.63E−09 | 1.89 | 2.63E−09 | 10.1 |
| miR-335-3p | 2.64 | 2.22E−12 | 2.64 | 2.22E−12 | 6.1 |
| miR-345-5p | 1.79 | 6.07E−10 | 1.79 | 6.07E−10 | 8.3 |
| miR-34a-5p | 2.85 | 2.73E−14 | 2.85 | 2.73E−14 | 8.3 |
| miR-421 | 2.08 | 1.00E−08 | 2.08 | 1.00E−08 | 5.2 |
| miR-424-3p | 1.92 | 1.20E−07 | 1.92 | 1.20E−07 | 4.2 |
| miR-92a-3p | 1.64 | 7.89E−07 | 1.64 | 7.89E−07 | 15.8 |
| miR-95-3p | 2.40 | 5.50E−09 | 2.40 | 5.50E−09 | 4.8 |

CRC, colorectal cancer; AA, advanced adenoma, FC, fold change; FDR, false discovery rate.

TABLE 5

| | Clinical validation phase (n = 767)[1] | | | | | |
|---|---|---|---|---|---|---|
| | CRC (n = 67) vs. control (n = 217) | | AA (n = 347) vs. control (n = 217) | | NAA (n = 136) vs. control (n = 217) | |
| MicroRNA | P-value | AUC | P-value | AUC | P-value | AUC |
| miR-130b-3p | 1.06E−02 | 0.71 | 6.86E−03 | 0.69 | 2.64E−01 | 0.62 |
| miR-21-5p | 1.16E−01 | 0.69 | 6.15E−01 | 0.65 | 6.68E−01 | 0.59 |
| miR-221-3p | 7.26E−03 | 0.70 | 6.96E−01 | 0.64 | 7.24E−01 | 0.60 |
| miR-25-3p | 3.47E−02 | 0.70 | 1.42E−01 | 0.65 | 1.51E−01 | 0.61 |
| miR-27a-3p | 2.78E−02 | 0.69 | 4.86E−01 | 0.65 | 1.23E−01 | 0.61 |
| miR-39a-3p | 4.44E−02 | 0.69 | 2.70E−01 | 0.64 | 8.91E−02 | 0.60 |
| miR-335-3p | 5.77E−01 | 0.67 | 3.13E−01 | 0.65 | 1.64E−01 | 0.63 |
| miR-24a-5p | 7.30E−03 | 0.71 | 6.44E−01 | 0.64 | 7.94E−01 | 0.59 |
| miR-421 | 1.27E−06 | 0.77 | 1.18E−04 | 0.71 | 1.66E−01 | 0.61 |

CRC, colorectal cancer; AA, advanced adenoma; NAA, non-advanced adenoma; AUC: area under the receiver operating characteristics curve.
[1]Results were adjusted by age and gender.

TABLE 6

| | Clinical validation phase (n = 767)[1] Advanced neoplasm (n = 414) vs. non-advanced neoplasm (n = 353) | | | |
|---|---|---|---|---|
| MicroRNA | p-value | Sensitivity [2] | Specificity [2] | AUC |
| miR-130b-3p | 0.003 | 82 | 39 | 0.64 |
| miR-21-5p | ns | 72 | 48 | 0.62 |
| miR-221-3p | ns | 70 | 51 | 0.62 |
| miR-25-3p | ns | 72 | 47 | 0.62 |
| miR-27a-3p | 0.02 | 69 | 52 | 0.63 |
| miR-29a-3p | ns | 68 | 53 | 0.62 |

TABLE 6-continued

| Clinical validation phase (n = 767)[1] | | | |
|---|---|---|---|
| Advanced neoplasm (n = 414) vs. non-advanced neoplasm (n = 353) | | | |
| MicroRNA | p-value | Sensitivity[2] | Specificity[2] | AUC |
| miR-335-3p | ns | 74 | 45 | 0.62 |
| miR-34a-5p | ns | 71 | 49 | 0.62 |
| miR-421 | 0.0001 | 81 | 43 | 0.68 |

AUC, area under the receiver operating characteristics curve; ns, not significant.
[1]Results were adjusted by age and gender.
[2] Sensitivity and specificity was calculated considering the optimal cut-point associated with the minimum error rate.

TABLE 7

| | Training set (n = 578) | | | | | | | Test set (n = 189) | | | | | | |
|---|---|---|---|---|---|---|---|---|---|---|---|---|---|---|
| Endpoint | AUC | 95% CI | | Sn² | Sp² | PPV² | NPV² | AUC | 95% CI | | Sn² | Sp² | PPV² | NPV² |
| Faecal miRNA-based predictive model | | | | | | | | | | | | | | |
| (AA + CRC)² | 0.74 | 0.70 | 0.78 | 0.74 | 0.63 | 0.40 | 0.88 | 0.63 | 0.55 | 0.71 | 0.67 | 0.60 | 0.34 | 0.85 |
| (AA + CRC)⁴ | 0.74 | 0.69 | 0.78 | 0.64 | 0.77 | 0.30 | 0.93 | 0.63 | 0.54 | 0.72 | 0.42 | 0.73 | 0.15 | 0.92 |
| (CRC)⁴ | 0.86 | 0.80 | 0.92 | 0.96 | 0.36 | 0.47 | 0.94 | 0.74 | 0.58 | 0.91 | 0.96 | 0.33 | 0.41 | 0.94 |
| (AA)⁴ | 0.71 | 0.66 | 0.76 | 0.61 | 0.71 | 0.47 | 0.81 | 0.64 | 0.54 | 0.74 | 0.59 | 0.69 | 0.41 | 0.83 |
| Faecal haemoglobin concentration-based predictive model | | | | | | | | | | | | | | |
| (AA + CRC)² | 0.61 | 0.57 | 0.66 | 0.60 | 0.59 | 0.32 | 0.81 | 0.62 | 0.54 | 0.70 | 0.62 | 0.58 | 0.27 | 0.85 |
| (AA + CRC)⁴ | 0.67 | 0.62 | 0.72 | 0.53 | 0.75 | 0.19 | 0.93 | 0.59 | 0.50 | 0.68 | 0.45 | 0.74 | 0.17 | 0.92 |
| (CRC)⁴ | 0.70 | 0.61 | 0.78 | 0.89 | 0.33 | 0.45 | 0.82 | 0.67 | 0.49 | 0.85 | 1.00 | 0.31 | 0.33 | 1.00 |
| (AA)⁴ | 0.64 | 0.59 | 0.69 | 0.50 | 0.68 | 0.45 | 0.72 | 0.59 | 0.49 | 0.69 | 0.43 | 0.63 | 0.33 | 0.72 |
| Combined faecal miRNA and haemoglobin concentration-based predictive model | | | | | | | | | | | | | | |
| (AA + CRC)² | 0.72 | 0.68 | 0.76 | 0.67 | 0.66 | 0.54 | 0.78 | 0.70 | 0.63 | 0.78 | 0.68 | 0.64 | 0.47 | 0.81 |
| (AA + CRC)⁴ | 0.74 | 0.69 | 0.78 | 0.63 | 0.79 | 0.40 | 0.91 | 0.67 | 0.58 | 0.76 | 0.48 | 0.75 | 0.22 | 0.90 |
| (CRC)⁴ | 0.90 | 0.86 | 0.94 | 0.96 | 0.48 | 0.70 | 0.90 | 0.93 | 0.87 | 0.99 | 0.97 | 0.43 | 0.63 | 0.94 |
| (AA)⁴ | 0.70 | 0.65 | 0.75 | 0.50 | 0.75 | 0.70 | 0.56 | 0.64 | 0.54 | 0.74 | 0.49 | 0.71 | 0.63 | 0.58 |

[1]MiRNA-based predictive model included miR-421 and miR-27a, along with age and gender.
[2]All parameters were calculated considering the optimal cut-point associated with the minimum error rate.
[3]Negative category: patients with non-advanced adenomas and individuals with normal colonoscopy.
[4]Negative category: individuals with normal colonoscopy.

For reasons of completeness, various aspects of the invention are set out in the following numbered clauses:

Clause 1. In vitro method for diagnosis or screening colorectal cancer and/or a pre-cancerous stage thereof which comprises: a) Measuring the expression level of at least miR-421, in a biological sample obtained from the subject and b) wherein the overexpression of miR-421, as compared with the reference expression level measured in healthy control subjects, is indicative that the subject is suffering from colorectal cancer and/or a pre-cancerous stage thereof.

Clause 2. The in vitro method of clause 1, which comprises: a) Measuring the expression level of at least the combination [miR-421 and miR-27a], [miR-421 and miR-25], [miR-421 and miR-221], [miR-421 and miR-34a], [miR-421 and miR-29a] or [miR-421 and miR-130b] in a biological sample obtained from the subject and b) wherein the overexpression at least the combination [miR-421 and miR-27a], [miR-421 and miR-25], [miR-421 and miR-221], [miR-421 and miR-34a], [miR-421 and miR-29a] or [miR-421 and miR-130b], as compared with the reference expression level measured in healthy control subjects, is indicative that the subject is suffering from colorectal cancer and/or a pre-cancerous stage.

Clause 3. The in vitro method of any one of the previous clauses, characterized in that it is performed in 50 to 75-years-old subjects.

Clause 4. The in vitro method of any one of the previous clauses, which further comprises determining the presence or concentration of haemoglobin preferably before the determination of the expression level of the miRNAs, wherein the presence or higher concentration of haemoglobin as compared with healthy control subjects, is indicative that the subject is suffering from colorectal cancer and/or a pre-cancerous stage.

Clause 5. The in vitro method of any one of the previous clauses, wherein the biological sample is stool sample, preferably a stool sample of less than 5 mg, preferably 2.5 mg.

Clause 6. The in vitro method of any one of the previous clauses, wherein the determination of the expression level of the miRNAs is carried out in the remaining stool samples which have been previously used for the determination of the presence or concentration of haemoglobin.

Clause 7. The in vitro method of any one of the previous clauses, wherein the pre-cancerous stage of colorectal cancer is advanced colorectal adenoma.

Clause 8. The in vitro method of any one of the previous clauses, wherein the diagnosis of the colorectal cancer and/or a pre-cancerous stage thereof is confirmed by an image technique, preferably colonoscopy.

Clause 9. In vitro use of at least miR-421 for the diagnosis or screening of colorectal cancer and/or a pre-cancerous stage thereof.

Clause 10. The in vitro use of clause 9, of at least [miR-421 and miR-27a], [miR-421 and miR-25], [miR-421 and miR-221], [miR-421 and miR-34a], [miR-421 and miR-29a] or [miR-421 and miR-130b] for the diagnosis or screening of colorectal cancer and/or a pre-cancerous stage thereof.

Clause 11. Kit of parts comprising:
a. Means or reagents for the determination of the presence or concentration of haemoglobin; and
b. Means or reagents for the determination of the expression level of miR-421.

Clause 12. The kit of parts of clause 11, comprising:
a. Means or reagents for the determination of the presence or concentration of haemoglobin; and
b. Means or reagents for the determination of the expression level of [miR-421 and miR-27a], [miR-421 and miR-25], [miR-421 and miR-221], [miR-421 and miR-34a], [miR-421 and miR-29a] or [miR-421 and miR-130b].

Clause 13. The kit of parts of any one of clauses 11 or 12, wherein the determination of the presence or concentration of haemoglobin is carried out by using antibodies specific to human haemoglobin and the determination of the expression level of miRNAs is carried out by qRT-PCR.

Clause 14. Use of the kit of any one of clauses 11 to 13 for diagnosis or screening colorectal cancer and/or a pre-cancerous stage thereof.

Clause 15. The use of the kit of clause 14, for diagnosis or screening advanced colorectal adenoma.

The invention claimed is:

1. An in vitro method for diagnosis or screening colorectal cancer or a pre-cancerous advanced colorectal adenoma in a subject at risk, comprising: a) measuring the expression level of at least miR-421 in a biological sample obtained from the subject at risk, wherein the biological sample is a stool sample; (b) identifying the subject at risk as being a subject suffering from colorectal cancer and/or a pre-cancerous advanced colorectal adenoma based on a risk score that is generated by comparing the expression level of the at least miR-421 to a reference expression level as measured in healthy control subjects, wherein a positive risk score is obtained from a finding of an overexpression of at least the miRNA-421; and (c) subjects having a positive risk score from step (b), conducting an imaging technique on the subject suffering from colorectal cancer and/or a pre-cancerous advanced colorectal adenoma to confirm a positive diagnosis of colorectal cancer or a pre-cancerous advanced colorectal adenoma.

2. The in vitro method, according to the claim 1, which comprises: a) measuring the expression level of at least one combination of [miR-421 and miR-27a], [miR-421 and miR-25], [miR-421 and miR-221], [miR-421 and miR-34a], [miR-421 and miR-29a] or [miR-421 and miR-130b] in the biological sample; (b) identifying the subject at risk as being a subject suffering from colorectal cancer or a pre-cancerous advanced colorectal adenoma based on a risk score that is generated by comparing the expression level of the at least one combination to reference expression levels as measured in healthy control subjects and wherein a positive risk score is obtained from a finding of an overexpression of the at least one combination.

3. The in vitro method, according to claim 1, wherein the subject at risk is from 50 to 75-years-old.

4. The in vitro method, according to claim 1, which further comprises determining the presence or concentration of haemoglobin, wherein the presence or higher concentration of haemoglobin as compared with healthy control subjects is indicative that the subject at risk is suffering from colorectal cancer or pre-cancerous advanced colorectal adenoma.

5. The in vitro method, according to claim 1, wherein the stool sample is less than 5 mg.

6. The in vitro method, according to claim 1, wherein the measuring of the expression level of the at least miRNA-421 is carried out in a stool sample which has been previously used for the determination of the presence or concentration of haemoglobin.

7. The in vitro method, according to claim 1, wherein the imaging technique is a colonoscopy.

8. The in vitro method according claim 1, which further comprises determining the presence or concentration of haemoglobin, wherein the presence or higher concentration of haemoglobin as compared with healthy control subjects, is indicative that the subject at risk is suffering from colorectal cancer or a pre-cancerous advanced colorectal adenoma, and wherein the stool sample is less than 5 mg.

9. The method of claim 1, further comprising collecting a stool sample prior to measuring the expression level.

10. The method of claim 1, further comprising treating the subject for a cancer or for a pre-cancerous lesion by endoscopic polypectomy, surgical resection, chemotherapy, or radiotherapy.

11. The in vitro method, according to claim 5, wherein the stool sample is less than 2.5 mg.

12. An in vitro method for diagnosis or screening colorectal cancer or a pre-cancerous advanced colorectal adenoma in a subject at risk, comprising (a) collecting a stool sample from the subject at risk; (b) measuring the expression level of at least miR-421 in the stool sample; (c) identifying the subject at risk as being a subject suffering from colorectal cancer or a pre-cancerous advanced colorectal adenoma based on a risk score that is generated by comparing the expression level of the at least miR-421 to a reference expression level as measured in healthy control subjects, and wherein a positive risk score is obtained from a finding of an overexpression of at least the miRNA-421; and (d) conducting an imaging technique on the subject suffering from colorectal cancer or a pre-cancerous advanced colorectal adenoma to confirm a positive diagnosis of colorectal cancer or a pre-cancerous advanced colorectal adenoma.

13. The in vitro method of claim 12, further comprising determining the presence or concentration of haemoglobin in the stool sample, wherein when both haemoglobin is present or is present at an increased concentration as compared with healthy control subjects and the miR-421 is overexpressed as compared with healthy control indicates that the subject at risk is suffering from colorectal cancer or a pre-cancerous advanced colorectal adenoma.

14. The in vitro method, according to the claim 12, which comprises: (a) measuring the expression level of at least one combination of [miR-421 and miR-27a], [miR-421 and miR-25], [miR-421 and miR-221], [miR-421 and miR-34a], [miR-421 and miR-29a] or [miR-421 and miR-130b] in the stool sample, and (b) identifying the subject at risk as being a subject suffering from colorectal cancer or a pre-cancerous advanced colorectal adenoma based on a risk score that is generated by comparing processing the expression level of the at least one combination to reference expression levels as measured in healthy control subjects and wherein a positive risk score is obtained from a finding of an overexpression of the at least the one combination.

15. The in vitro method of claim 14, further comprising determining the presence or concentration of haemoglobin in the stool sample, wherein when both haemoglobin is present or is present at an increased concentration as compared with healthy control subjects and the at least one combination of miRNAs is overexpressed as compared with healthy control subjects indicates that the subject at risk is suffering from colorectal cancer or a pre-cancerous advanced colorectal adenoma.

16. The in vitro method of claim 10, further comprising determining the presence or concentration of haemoglobin in the stool sample, wherein when both haemoglobin is present or is present at an increased concentration as compared with healthy control subjects and the miR-421 is overexpressed as compared with healthy control indicates that the subject at risk is suffering from colorectal cancer or a pre-cancerous advanced colorectal adenoma.

17. The in vitro method, according to the claim 10, which comprises: (a) measuring the expression level of at least one combination of [miR-421 and miR-27a], [miR-421 and miR-25], [miR-421 and miR-221], [miR-421 and miR-34a], [miR-421 and miR-29a] or [miR-421 and miR-130b] in the stool sample, and (b) identifying the subject at risk as suffering from colorectal cancer or a pre-cancerous advanced colorectal adenoma based on a risk score that is generated by comparing the expression level of the at least one combination to reference expression levels as measured in healthy control subjects and wherein a positive risk score is obtained from a finding of an over expression of the at least one combination.

* * * * *